(12) United States Patent
Hoefinghoff et al.

(10) Patent No.: US 9,162,006 B2
(45) Date of Patent: Oct. 20, 2015

(54) HEMOSTATIC SPONGE

(75) Inventors: Joris Hoefinghoff, Vienna (AT); Hans Christian Hedrich, Vienna (AT)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 486 days.

(21) Appl. No.: 12/816,645

(22) Filed: Jun. 16, 2010

(65) Prior Publication Data

US 2010/0318048 A1 Dec. 16, 2010

Related U.S. Application Data

(60) Provisional application No. 61/187,576, filed on Jun. 16, 2009.

(51) Int. Cl.
*A61F 13/36* (2006.01)
*A61L 15/42* (2006.01)
*A61L 15/32* (2006.01)
*A61L 15/58* (2006.01)
*A61L 15/26* (2006.01)
*A61L 15/44* (2006.01)
*A61L 15/64* (2006.01)

(52) U.S. Cl.
CPC .............. *A61L 15/425* (2013.01); *A61L 15/26* (2013.01); *A61L 15/32* (2013.01); *A61L 15/325* (2013.01); *A61L 15/44* (2013.01); *A61L 15/58* (2013.01); *A61L 15/64* (2013.01); *A61L 2300/418* (2013.01); *A61L 2400/04* (2013.01)

(58) Field of Classification Search
CPC ............ A61F 13/0206; A61F 13/0209; A61F 13/0253; A61F 13/00004–13/00046; A61F 13/0203; A61F 13/0213; A61F 13/022; A61F 13/0223; A61F 13/0246–13/0256; A61F 2013/00089–13/00361; A61F 2013/00463–13/00472; A61L 15/16–15/34; A61L 15/425; A61L 15/44; A61L 15/58; A61L 15/64; A61L 2300/418; A61L 2400/04
USPC ........................................................ 604/365
See application file for complete search history.

(56) References Cited

U.S. PATENT DOCUMENTS

| | | | |
|---|---|---|---|
| 2,507,244 A | 5/1950 | Correll | |
| 2,558,395 A | 6/1951 | Studer | |
| 4,013,078 A | 3/1977 | Feild | |
| 4,124,705 A | 11/1978 | Rothman et al. | |
| 4,164,559 A | 8/1979 | Miyata et al. | |
| 4,179,400 A | 12/1979 | Tsao et al. | |
| 4,265,233 A | 5/1981 | Sugitachi et al. | |
| 4,291,013 A | 9/1981 | Wahlig et al. | |
| 4,292,972 A | 10/1981 | Pawelchak et al. | |
| 4,298,598 A | 11/1981 | Schwarz et al. | |
| 4,300,494 A | 11/1981 | Graiff et al. | |
| 4,347,234 A | 8/1982 | Wahlig et al. | |
| 4,362,567 A | 12/1982 | Schwarz et al. | |
| 4,377,572 A | 3/1983 | Schwarz et al. | |
| 4,412,947 A * | 11/1983 | Cioca | 530/356 |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |
| 4,543,332 A | 9/1985 | Jao et al. | |
| 4,554,156 A | 11/1985 | Fischer et al. | |
| 4,600,574 A | 7/1986 | Lindner et al. | |
| 4,640,834 A | 2/1987 | Eibl et al. | |
| 4,655,211 A | 4/1987 | Sakamoto et al. | |
| 4,746,514 A | 5/1988 | Warne | |
| 4,749,689 A | 6/1988 | Miyata et al. | |
| 4,803,075 A | 2/1989 | Wallace et al. | |
| 4,818,517 A | 4/1989 | Kwee et al. | |
| 4,832,686 A | 5/1989 | Anderson | |
| 4,837,285 A | 6/1989 | Berg et al. | |
| 4,891,359 A | 1/1990 | Saferstein et al. | |
| 4,925,677 A | 5/1990 | Feijen | |
| 4,946,870 A | 8/1990 | Partain, III. et al. | |
| 5,007,916 A | 4/1991 | Linsky et al. | |
| 5,017,229 A | 5/1991 | Burns et al. | |
| 5,023,082 A | 6/1991 | Friedman et al. | |
| 5,041,292 A | 8/1991 | Feijen | |
| 5,061,274 A | 10/1991 | Kensey | |
| 5,061,492 A | 10/1991 | Okada et al. | |
| 5,080,893 A | 1/1992 | Goldberg et al. | |
| 5,108,421 A | 4/1992 | Fowler | |

(Continued)

FOREIGN PATENT DOCUMENTS

| | | |
|---|---|---|
| EP | 0132983 A | 2/1985 |
| EP | 0376931 | 7/1990 |
| EP | 0132983 B2 | 6/1991 |
| EP | 0493387 | 7/1992 |
| EP | 0568334 A1 | 11/1993 |

(Continued)

OTHER PUBLICATIONS

Ansell et al., "Gelfoam and Autologous Clot Embolization: Effect on Coagulation", *Invest. Radiol.* (1978) 13:115-120.

Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).

(Continued)

*Primary Examiner* — Philip R Wiest
*Assistant Examiner* — Benjamin Klein
(74) *Attorney, Agent, or Firm* — Kilpatrick Townsend & Stockton LLP

(57) ABSTRACT

The present invention provides a hemostatic porous sponge comprising a matrix of a fibrous biomaterial and particles of a fluid absorbing, particulate material adhered to said matrix material, a method of producing these sponges and their use for wound healing.

29 Claims, No Drawings

(56) References Cited

U.S. PATENT DOCUMENTS

| | | |
|---|---|---|
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Alleyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,722,943 A * | 3/1998 | Sessions ................... 602/57 |
| 5,853,749 A | 12/1998 | Hobbs |
| 5,874,500 A | 2/1999 | Rhee et al. |
| 5,891,558 A * | 4/1999 | Bell et al. ................. 428/218 |
| 5,902,832 A | 5/1999 | Van Bladel et al. |
| 5,908,054 A | 6/1999 | Safabash et al. |
| 5,931,165 A | 8/1999 | Reich et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A * | 12/2000 | Rhee et al. ................ 525/54.1 |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |
| 6,458,889 B1 | 10/2002 | Trollsas et al. |
| 6,624,245 B2 | 9/2003 | Wallace et al. |
| 6,706,690 B2 * | 3/2004 | Reich et al. ................ 424/484 |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 8,206,448 B2 | 6/2012 | Burkinshaw et al. |
| 2002/0193448 A1 | 12/2002 | Wallace et al. |
| 2003/0064109 A1 | 4/2003 | Qian et al. |
| 2006/0106364 A1 | 5/2006 | Whitlock et al. |
| 2006/0147492 A1 | 7/2006 | Hunter et al. |
| 2006/0165762 A1 * | 7/2006 | Plaut et al. ................ 424/445 |
| 2006/0167561 A1 | 7/2006 | Odar et al. |
| 2006/0193846 A1 | 8/2006 | Stimmeder |
| 2008/0085316 A1 | 4/2008 | Qian et al. |
| 2008/0091277 A1 | 4/2008 | Deusch et al. |
| 2008/0187591 A1 | 8/2008 | Rhee et al. |
| 2008/0286376 A1 | 11/2008 | Qian et al. |
| 2009/0142396 A1 | 6/2009 | Odar et al. |
| 2010/0028309 A1 | 2/2010 | Odar et al. |
| 2010/0292717 A1 | 11/2010 | Petter-Puchner et al. |
| 2011/0202026 A1 | 8/2011 | Hedrich et al. |
| 2011/0251574 A1 | 10/2011 | Hedrich et al. |

FOREIGN PATENT DOCUMENTS

| | | |
|---|---|---|
| EP | 0891193 | 1/1999 |
| EP | 0612252 B1 | 5/1999 |
| EP | 1084720 A1 | 3/2001 |
| EP | 1283063 A1 | 2/2003 |
| EP | 1462123 A1 | 9/2004 |
| EP | 1484070 A1 | 12/2004 |
| EP | 1690553 A1 | 8/2006 |
| EP | 01414370 B1 | 4/2007 |
| JP | 59-113889 | 6/1984 |
| JP | 05308969 | 11/1993 |
| JP | 6-254148 | 9/1994 |
| JP | 9-504719 | 5/1997 |
| JP | 07090241 | 4/2007 |
| KR | 10-1991-0007847 B1 | 10/1991 |
| WO | WO 86/00912 | 2/1986 |
| WO | WO 90/13320 A1 | 11/1990 |
| WO | WO 92/21354 | 12/1992 |
| WO | 93/21908 | 11/1993 |
| WO | WO 94/27630 A1 | 12/1994 |
| WO | WO 95/12371 | 5/1995 |
| WO | WO 92/22252 | 6/1995 |
| WO | WO 95/15747 | 6/1995 |
| WO | WO 96/04025 | 2/1996 |
| WO | WO 96/06883 | 3/1996 |
| WO | WO 96/10374 | 4/1996 |
| WO | WO 96/10428 | 4/1996 |
| WO | WO 96/14368 | 5/1996 |
| WO | WO 96/39159 | 12/1996 |
| WO | WO 97/37694 A1 | 10/1997 |
| WO | WO 98/08550 A1 | 3/1998 |
| WO | WO 99/13902 A1 | 3/1999 |
| WO | WO 02/22184 A2 | 3/2002 |
| WO | WO 02-070594 A2 | 9/2002 |
| WO | WO 03/007845 A1 | 1/2003 |
| WO | 03/899022 A1 | 10/2003 |
| WO | WO 2004/108179 A1 | 12/2004 |
| WO | WO 2006/031358 A | 3/2006 |
| WO | 2008-074331 A1 | 6/2006 |
| WO | WO 2006/118460 A1 | 11/2006 |
| WO | WO 2007/001926 A2 | 1/2007 |
| WO | WO 2007/137839 A2 | 12/2007 |
| WO | WO 2007/137839 A3 | 12/2007 |
| WO | WO 2008/016983 A2 | 2/2008 |
| WO | WO 2008016983 A2 * | 2/2008 |

OTHER PUBLICATIONS

Barton et al., "Fibrin Glue as a Biologic Vascular Patch—A Comparative Study" (abstract posted at http://www.ncbi.nlm.nih.gov/ on Jan. 3, 2001 from) *J. Surg. Res.* (1986) 40(5): 510-513.

Baxter product brochure for TissuFleece E, TissuCone E and TissuFoil E (2003).

Baxter Product Catalogue; Collagen; 4 pages (2006).

(56) References Cited

OTHER PUBLICATIONS

Boyers et al., "Reduction of Postoperative Pelvic Adhesions in the Rabbit with Gore-Tex Surguical Membrane" *Fen. Ster.* (1988) 49(6):1066--1070.
Bruck, S. D., Ed., Controlled Drug Delivery, CRC Press, Boca Raton, FL (1983) A title page and table of contents.
Cantor et al., "Gelfoam and Thrombin in Gastrointestinal Bleeding: An Experimental Study", pp. 890-893.
Cantor et al., "Gelfoam and Thrombin in Treatment of Massive Gastroduodenal Hemmorhage: A Preliminary Report" *Am J. Surg.* (1950) pp. 883-887.
Cantor et al., "Gelfoam and Thrombin in Treatment of Massive Upper Gastroduodenal Hemorrhage", *Am. J. Surg.* (1951) pp. 230-235.
Chaplin, J.M., et al.; "Use of an Acellular Dermal Allograft for Dural Replacement: An Experimental Study"; Neurosurgery: vol. 45:2; pp. 320-327 (Aug. 1999).
Chuang et al., "Sheath Needle for Liver Biopsy in High-Risk Patients", *Radiology* (1988) 166:261-262.
Collins et al., "Enemata of Gelfoam-Milk Suspension Combined with Thrombin Solution to Control Massive Hemorrhage Following Anorectal Surgery", *Am. J. Proctol.* (1951) 2:60-63.
Collins, Ronald et al., "Use of Collagen Film as a Dural Substitute: Preliminary Animal Studies", Journal of Biomedical Materials Research, vol. 25, 267-276 (1991).
Edgerton et al., "Vascular Hamartomas and Hemangiomos: Classification and Treatment" *Southern Med. J.* (1982) 75(12):1541-1547.
Filippi, R., et al.; "Bovine Pericardium for Duraplasty: Clinical Results in 32 Patients"; Neurosurg. Rev.; vol. 20; pp. 103-107 (2001).
GentaFleece Kollagenvlies Version 5 found on internet at: http://www.advancingbiosurgery.com/en_EU/downloads/ifu_gentafleece.pdf, Mar. 2002, 2 pages.
Heller et al., "Release of Norethindrone from Poly(Ortho Esters)" *Polymer Engineering Sci.* (1981) 21:727-731.
Hieb, Lee D. et al., "Spontaneous Postoperative Cerebrospinal Fluid Leaks Following Application of Anti-Adhesion Barrier Gel", SPINE vol. 26, No. 7, pp. 748-751, 2001.
Hood et al., "Efficacy of Topical Hemostat Floseal Matrix in Vascular Surgery," 24th World Congress of the International Society for Cardiovascular Surgery (Sep. 12-16, 1999), 2 pages total.
Hotz et al., "Collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.
Jeong et al., "Biodegradable Block Copolymers as Injectible Drig-Delivery Systems" *Nature* (1997) 388:860-862.
Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.
Kline, D.G.; "Dural Replacement with Resorbable Collagen"; Arch Surg; vol. 91; pp. 924-929 (Dec. 1965).
Knopp U., "A new collagen foil versus a cadaveric dura graft for dural defects-a comparative animal experimental study", EANS—12th European Congress of Neurosurgery, Lisbon, Sep. 7-12, 2003, 663-666.
Krill et al., "Topical Thrombin and Powdered Gelfoam: An Efficiaent Hemostatic Treatment for Surgery", *J. Tenn. Dent. Assoc.* (1986) 66(2):26-27.
Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.
Langer et al., "Chemical and Physical Structure of Polymerns as Carriers for Controlled Release of Bioactive Agents: A Review" *Rev. Marco Chem. Phys.* (1983) C23(1):61-126.
Laquerriere, A., et al.; "Experimental Evaluation of Bilayered Human Collagen as a Dural Substitute"; J. Neurosurg; vol. 78; pp. 487-491 (Mar. 1993).

Le, Anh X. et al., "Unrecognized Durotomy After Lumbar Discectomy: A Report of Four Cases Associated with the Use of ADCON-L", SPINE vol. 26, No. 1, pp. 115-118, 2001.
Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).
Leong et al., "Polyanhydrides for Controlled Release of Bioactive Agents" *Biomaterials* (1986) 7:364-371.
Leong et al., "Polymeric Controlled Drug Delivery" *Adv. Drug Delivery Rev.* (1987)1:199-233.
Maok, "Hemostatic Agents" (1991) *Today's O.R. Nurse*, pp. 6-10.
Masar et al., "Synthesis of Polyurethanes and Investigation of their Hydrolytic Stability" *J. Polymer. Sol.*, Polymer Symposium (1979) 66:259-268.
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448- 452 (Sep. 1985).
McClure et al., "Massive Gastroduodenal Hemorrhage: Treatment with Powdered Gelfoam and Buffered Thrombin Solution" *Surg.* (1952) 32:630-637.
Meddings, N., et al.; "Collagen Vicryl—A New Dural Prosthesis"; Acta Neurochir; vol. 117; pp. 53-58 (1992).
Mello, L.R., et al.; "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al.; "Experimental Evaluation of Collagen Sponge as a Dural Graft"; British Journal of Neurosurgery; vol. 7; pp. 635-641 (1993).
O'Neill, P., et al.; "Use of Porcine Dermis as Dural Substitute in 72 Patients"; J. Neurosurg.; vol. 61; pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery.; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
PCT International Preliminary Report on Patentability and Written Opinion mailed Feb. 17, 2009, International Application No. PCT/US2007/074984, 8 pages.
Pietrucha, K.; "New Collagen Implant as Dural Substitute"; Biomatarials; vol. 12; pp. 320-323 (Apr. 1991).
Pitt et al., "Controlled Release of Bioactive Materials", R. Baker, Ed., Academic Press, New York, 1980.
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (NEURO-PATCH®) Comme Substitut Dural"; Neurochirugie; vol. 49:2-3; pp. 83-89 (2003), English abstract only on p. 83.
Raul, J.S., et al.; "Utilisation du Polyester Urethane (NEURO-PATCH®) Comme Substitut Dural"; Neurochirugie; vol. 49:2-3; pp. 83-89 (2003).
Reddy, M., et al.; "A Clinical Study of a Fibrinogen-Based Collagen Fleece for Dural Repair in Neurosurgery"; Acta Neurochir; vol. 144; pp. 265-269 (2002).
Riley et al., "Percutaneous Liver Biopsy with Plugging of Needle Track: A Safe Method for Use in Patients with Impaired Coagulation" *Lancet* (Aug. 25, 1984) pp. 436.
Ross, Jeffrey S. et al., "Association Between Peridural Scar and Recurrent Radicular PAIN After Lumbar Discectomy: Magnetic Resonance Evaluation", Neurosurgery, pp. 855-863, 1996.

(56) References Cited

OTHER PUBLICATIONS

San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation ofDural Closure in 134 Patients"; Neurosurgery; vol. 26:2; pp. 207-210 (1990).
Sidman et al., "Biodegradable, Implantable Sustained Release Systems Based on Glutamic Acid Copolymers" *J. Membrane Science* (1979) 7:227-291.
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; Akt. Traumata!; vol. 15; pp. 120-121 (1985), English abstract only on p. 120.
Springorum, H.W.; "Die Verwendung von Kollagenfolien zur Uberbruckung von Defekten des Gleitgewebes bei Achillotenotomien und Achillessehnenrupturen"; Akt. Traumata!; vol. 15; pp. 120-121 (1985).
Stricker, A., et al.; "Die Verwendung von TissuFoil Membran bei der Sinusbodenaugmentation"; Ellipse; vol. 17:1; pp. 1-5 (2001), English abstract only on p. 1.
Stricker, A., et al.; "Die Verwendung von TissuFoil Membran bei der Sinusbodenaugmentation"; Ellipse; vol. 17:1; pp. 1-5 (2001).
Sugitachi et al., "A Newly Devised Chemo-embolic Agent, G.T. XIII-ADM." (English abstract posted at http://www.ncbi.nlm.nih.gov/ on Jan. 3, 2001 from) *Gan. To. Kagaku Ryoho.* (1985) 12(10) 1942-1943.
Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.
Sugitachi et al., "Preoperative Transcatheter Arterial Chemoembolization for Locally Advanced Breast Cancer: Application for New Thrombotic Materials" *Japan J. Surg.* (1983) 13(5):456-458.
T. Kofidis et al., "Clinically established Hemostatis Scaffold (Tissue Fleece) as Biomatrix in Tissue- and organ-engineering research", Tissue Eng vol. 9, No. 3, 2003, S.517-523; ISSN: 1076-3279.
TissuFleece E found on internet at: http://www.biosurgery.de/Produkte/pdf/TissuFleece E_GI.pdf, Feb. 2003, 2 pages.
Tobin et al., "Plugged Liver Biopsy in Patients with Impaired Coagulation" *Digestive Diseases and Science* (1989) 34(1):13-15.
Tucker et al., "Absorbable Gelatin (Gelfoam) Sponge" Charles T. Thomas, Publisher, Springfiled, Illinois, 3-125.
Vander Salm et al., "Reduction of Sternal Infection by Application of Topical Vancomycin" *J. Thorac. Surg.* (1989) 98:618-622.
Vinas, F.E., et al.; "Evaluation of Expanded Polytetrafluoroethylene (ePTFE) versus Polydioxanone (PDS) for the Repair ofDura Mater Defects"; Neurological Research; vol. 21; pp. 262-268 (Apr. 1999).
Warren, W.L., et al.; Dural Repair Using Acellular Human Dermis: Experience with 200 Cases: Technique Assessment.; Neurosurgery; vol. 46:6; pp. 1391-1396 (Jun. 2000).
Yuki et al., "Effects of EndoscopicVariceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral.* Japan (1990) 25(5):561-567.
Ziegelaar, B.W.; "Tissue Engineering of a Tracheal Equivalent", Doctoral Thesis at Ludwig Maximilians University, Munich, Germany; 25 pages (2004).
Ziegelaar, BW et al., "The characterisation of human respiratory epithelial cells cultured on reabsorbable scaffolds: first steps towards a tissue engineered tracheal replacement", Biomaterials 23 (2002), 1425-1438; ISSN 0142-9612.
Zins et al., "US-Guided Percutaneous Liver Biopsy with Plugging of the Needle Track: A Prospective Study in 72 High-Rish Patients" *Radiology* (1992) 184(3):841-843.
Cheung, David T., et al., "Mechanism of crosslinking of proteins by glutaraldehyde IV: in Vitro and in Vivo stability of a crosslinked collagen matrix", Connective Tissue Research, 1990;25(1), pp. 27-34.
Jonas, Richard A., et al., "A new sealant for knitted Dacron prostheses: Minimally cross-linked gelatin", J. Vasc. Surg., Mar. 1988;7(3), pp. 414-419.
Larson, Paul O., "Topical Hemostatic Agents for Dermatologic Surgery", J. Dermatol. Surg. Oncol., Jun. 1988;14(6), pp. 623-632.
McPherson, J. M. et al., "An examination of the biologic response to injectable, glutaraldehyde cross linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.
McPherson, John M., et al., "The Effects of Heparin on the Physiochemical Properties of Reconstituted Collagen", Coll. Relat. Res., Jan. 1988;8(1), pp. 65-82.
Nimni, M. E., et al., "Chemically modified collagen: a natural biomaterial for tissue replacement", J. Biomed. Mater. Res., Jun. 1987;21(6), pp. 741-771.
Nimni, Marcel E., "The cross-linking and structure modification of the collagen matrix in the design of cardiovascular prosthesis", J. of Cardiac Surgery, Dec. 1988;3(4), pp. 523-533.
Rosenblatt, Joel, et al., "Effect of electrostatic forces on the dynamic rheological properties of injectable collagen biomaterials", Biomaterials, 1992;13(12), pp. 878-886.
Rosenblatt, Joel, et al., "Injectable collagen as a pH-sensitive hydrogel", Biomaterials, Oct. 1994;15(12), pp. 985-995.
Rossler, B., et al., "Collagen microparticles: preparation and properties", J. Microencapsulation, Jan.-Feb. 1995;12(1), pp. 49-57.
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.
Japanese Office Action mailed Jun. 4, 2014 for Japanese Patent Application No. 2012-515391 filed Jun. 16, 2010, all pages.

\* cited by examiner

HEMOSTATIC SPONGE

CROSS-REFERENCES TO RELATED APPLICATIONS

This application is a nonprovisional of, and claims the benefit of the filing date of U.S. Provisional Patent Application No. 61/187,576, entitled "HEMOSTATIC SPONGE, filed Jun. 16, 2009, the entire disclosure of which is incorporated herein by reference for all purposes.

BACKGROUND OF THE INVENTION

Biological glues based on coagulation factors of human or animal origin have long been known. A method for producing tissue adhesives based on fibrinogen and factor XIII has been described in U.S. Pat. No. 4,362,567, U.S. Pat. No. 4,298,598 and U.S. Pat. No. 4,377,572. The tissue adhesives are usually applied together with a separate component containing thrombin, which is enzymatically acting on fibrinogen to form fibrin, and on factor XIII to form the active factor XIIIa, which cross-links the fibrin to obtain a stable fibrin clot.

Collagen pads have been used for many years to improve wound healing or to stop bleeding. Their mechanism of action in hemostasis is based on platelets aggregation and activation, the formation of thrombin on the surface of activated platelets and the formation of a hemostatic fibrin clot by the catalytic action of thrombin on fibrinogen. To improve the hemostatic action of collagen pads or sheets it has been suggested to include factors of hemostasis within such pads.

In U.S. Pat. No. 4,600,574 a tissue adhesive based on collagen combined with fibrinogen and factor XIII is described. This material is provided in the lyophilized form, ready for use. The fibrinogen and factor XIII are combined with the collagen by impregnating the collageneous flat material with a solution comprising fibrinogen and factor XIII, and lyophilizing said material. The WO 97/37694 discloses a hemostatic sponge based on collagen and an activator or proactivator of blood coagulation homogeneously distributed therein. This sponge is provided in a dry form; which could be air-dried or lyophilized. However, it still contains a water content of at least 2%. U.S. Pat. No. 5,614,587 discusses bioadhesive compositions comprising collagen cross-linked using a multifunctionally activated synthetic hydrophilic polymer, as well as methods of using such compositions to effect adhesion between a first surface and a second surface, wherein at least one of the first and second surfaces can be a native tissue surface.

Collagen-containing compositions which have been mechanically disrupted to alter their physical properties are described in U.S. Pat. No. 5,428,024, U.S. Pat. No. 5,352,715, and U.S. Pat. No. 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 μm to 850 μm which may be suspended in water and which has a particular surface charge density is described in WO 96/39159. A collagen preparation having a particle size from 1 μm to 50 μm useful as an aerosol spray to form a wound dressing is described in U.S. Pat. No. 5,196,185. Other patents describing collagen compositions include U.S. Pat. No. 5,672,336 and U.S. Pat. No. 5,356,614.

SUMMARY OF THE INVENTION

The subject of the invention is a hemostatic porous sponge comprising a matrix of a fibrous biomaterial and particles of a fluid absorbing particulate material adhered to said matrix material. It has been found that previous pads of fibrous biomaterials, in particular collagen pads, for wound healing failed to induce hemostasis at conditions with impaired hemostasis (e.g. after heparinization). The inventive use of a particulate material within a matrix of collagen improves hemostasis in comparison to hemostasis without fluid absorbing particulate material. Without being limited to a certain theory, it appears that when using particles with a high capability to absorb liquids, a high concentration of clotting factors present in blood can be achieved which favors hemostasis. It is difficult to apply such particles directly onto the bleeding wound because the particles tend to flow away with the bloodstream. The incorporation of such particles in a hemostatic sponge allows a local fixation of such particles and further improves the hemostatic action of the sponge.

A further aspect relates to a method of manufacturing a hemostatic porous sponge comprising providing a fluid of a fibrous biomaterial and suspended particles of a fluid absorbing, particulate material, and drying said fluid with the suspended particles, thereby obtaining a hemostatic porous sponge comprising a matrix of a fibrous biomaterial and particles of a fluid absorbing, particulate material adhered to said matrix material. A hemostatic porous sponge obtainable by this method is comprised by the present invention. The term "fluid" according to the present invention includes a solution, a suspension or a gel.

Also provided is a kit for preparing a wound coverage, comprising a sponge as herein disclosed and pharmaceutically active substances. This kit and its components are in particular for the manufacture of a medical sponge for the treatment of an injury.

The person skilled in the art will readily understand that all preferred embodiments disclosed in the following are examples of specific embodiments, but are not necessarily limiting the general inventive concept. Furthermore, all special embodiments can be read on all inventive aspects and embodiments in any combination, if not mutually exclusive. All equivalents or obvious alterations or modifications as recognized by the skilled person are included by the present invention.

DETAILED DESCRIPTION OF THE INVENTION

The object of the invention is a hemostatic sponge based on a fibrous biomaterial with improved hemostatic properties. This goal is achieved by providing a fluid absorbing, particulate material adhered to the sponge. The fibrous biomaterial may support any hemostatic or blood clotting actions. This effect can be strengthened by the inventive particulate material. These particles are adhered to the fibrous biomaterial to provide a sufficiently strong fixation of the particles, increasing shelf life and increasing durability during usage, in particular as wound coverage where mechanic tensions can lead to unwanted detachment of the particles. The term "adhered" according to the present invention means that the particles are distributed within or embedded in or entrapped in the fibrous biomaterial. The particles may be held in the matrix material in any ordered or disordered state, preferably being homogeneously distributed therein. The sponge is a porous network of a fibrous biomaterial able to absorb body fluids when applied on an injury. Furthermore, the sponge is usually flexible and suitable to apply on diverse tissues and locations with various shapes.

The terms "sponge" and "pad" are used interchangeably within the meaning of the present invention.

Preferably the fibrous biomaterial is collagen, a protein, a biopolymer, or a polysaccharide.

The collagen used for the present invention can be from any collagen suitable to form a gel, including a material from liquid, pasty, fibrous or powdery collagenous materials that can be processed to a porous or fibrous matrix. The preparation of a collagen gel for the production of a sponge is e.g. described in the EP 0891193 (incorporated herein by reference) and may include acidification until gel formation occurs and subsequent pH neutralisation. To improve gel forming capabilities or solubility the collagen may be (partially) hydrolyzed or modified, as long as the property to form a stable sponge when dried is not diminished.

The collagen or gelatin of the sponge matrix is preferably of animal origin, preferably bovine or equine. However, also human collagen might be used in case of a hypersensitivity of the patient towards xenogenic proteins. The further components of the sponge are preferably of human origin, which makes the sponge suitable especially for the application to a human.

In a preferred embodiment the matrix material of the fibrous biocompatible polymer which forms the porous network of the sponge constitutes of between 1-50%, 1-10%, or about 3% of the dried porous sponge (w/w-%).

The particulate material in general is not soluble, in particular not water-soluble. It remains particulate in water. However the particles may be porous and/or hygroscopic and are allowed to swell. "Fluid absorbing" shall be considered as the physical process to hold fluids upon contacting which may or may not provoke swelling of the particles. Preferably the particles can hold an amount of a fluid, in particular blood, of at least 1 time, at least 2 times, at least 4 times or at least 10 times and/or up to 100 times, up to 20 times or up to 10 of the dry weight of the sponge. The particulate material according to the present invention can take up fluids even under pressure. To improve stability and adjust the swelling properties, the particulate material can be cross-linked.

The particulate material may be a hemostatic material and provide for the hemostatic action of the sponge alone or in combination with the sponge matrix. Hemostasis or any other clotting activity can be induced by activating the hemostatic system in a subject. The hemostatic sponge can increase the rate of hemostatic reactions as compared to hemostasis without treatment. This activation can be based on a multitude of reactions but usually includes catalytic processes of blood or serum proteins or oxidative processes. After initiation, the subject's hemostatic system usually proceeds with a strong enzymatic cascade leading to clotting. Such a catalysis or any other hemostatic activity can be initiated by the matrix material or the particulate material. Of course it is also possible to provided additional reactants or catalysts with the inventive sponge, such as an activator or proactivator of blood coagulation, including fibrinogen, thrombin or a thrombin precursor.

In preferred embodiments, particulate material is a polymer and/or a biomaterial, in particular a biopolymer. In order to facilitate recovery of the injury (in particular in the case of internal surgery where removal of any remaining foreign material may require addition surgery) it is preferred to use a bioresorbable particulate material.

The particulate material, the matrix material or the sponge as a whole can be biodegradable, being suitable for biological decomposition in vivo, or bioresorbable, i.e. able to be resorbed in vivo. Full resorption means that no significant extracellular fragments remain. A biodegradable material differs from a non-biodegradable material in that a biodegradable material can be biologically decomposed into units which may either be removed from the biological system and/or chemically incorporated into the biological system. In a preferred embodiment the particular material, the matrix material or sponge as a whole can be degraded by a subject, in particular a human subject, in less than 6 month, less than 3 month, less than 1 month, less than 2 weeks.

The particles can, e.g., be gelatin, gelatin derivatives, chemically derivatized gelatin, collagen, fibrin, proteins, polysaccharides or any mixture thereof, but other kinds of organic material can be used as well. Preferably, it is water-insoluble, biodegradeable and bioresorbable. Natural gelatin is cheap and broadly available and can be obtained from many sources. Gelatin is a hydrolysate of collagen. Convenient animal sources of gelatin and collagen include chicken, turkey, bovine, porcine, equine, or human sources. The collagen can also be artificial or recombinant collagen. Preferably, the gelatin is cross-linked to prevent complete solubility. Cross-linking may be achieved by incomplete hydrolysation of collagen or chemical cross-linking using cross-linking reagents such as formaldehyde or divalent aldehydes.

The particles according to the present invention are preferably microparticles being in the size range of micrometers. In preferred embodiments the particle size (average diameter in dry state) is 2000 µm or below. Even smaller particles may be used, e.g. of an average size below 1000 µm, or below 100 nm. Also possible is any size range within these borders, e.g. an average diameter of from 100 nm to 2000 µm in dry state.

Examples of such particles are e.g. described in U.S. Pat. No. 6,063,061 and U.S. Pat. No. 6,066,325 (both incorporated herein by reference).

After drying, the sponge may have a water content of at least 0.5 (percentages given in w/w here). In certain embodiments the sponge can be freeze-dried or air-dried.

Preferably, the sponge comprises an activator or proactivator of blood coagulation, including fibrinogen, thrombin or a thrombin precursor, as e.g. disclosed in U.S. Pat. No. 5,714,370 (incorporated herein by reference). Thrombin or the precursor of thrombin is understood as a protein that has thrombin activity and that induces thrombin activity when it is contacted with blood or after application to the patient, respectively. Its activity is expressed as thrombin activity (NIH-Unit) or thrombin equivalent activity developing the corresponding NIH-Unit. The activity in the sponge can be 500-5.000. In the following thrombin activity is understood to comprise both, the activity of thrombin or any equivalent activity. A protein with thrombin activity might be selected from the group consisting of alpha-thrombin, meizothrombin, a thrombin derivative or a recombinant thrombin. A suitable precursor is possibly selected from the group consisting of: prothrombin, factor Xa optionally together with phospholipids, factor IXa, activated prothrombin complex, FEIBA, any activator or a proactivator of the intrinsic or extrinsic coagulation, or mixtures thereof.

The hemostatic sponge according to the invention might be used together with further physiologic substances. For example, the sponge preferably further comprises pharmacologically active substances, among them antifibrinolytics, such as a plasminogen-activator-inhibitor or a plasmin inhibitor or an inactivator of fibrinolytics. A preferred antifibrinolytic is selected from the group consisting of aprotinin or an aprotinin derivative, alpha2-macroglobulin; an inhibitor or inactivator of protein C or activated protein C, a substrate mimic binding to plasmin that acts competitively with natural substrates, and an antibody inhibiting fibrinolytic activity.

As a further pharmacologically active substance an antibiotic, such as an antibacterial or antimycotic might be used together with the sponge according to the invention, preferably as a component homogeneously distributed in the sponge. Further bioactive substances such as growth factors and/or pain killers may be also present in the inventive sponge. Such a sponge Might be useful in e.g. wound healing. Further combinations are preferred with specific enzymes or enzyme inhibitors, which may regulate, i.e. accelerate or inhibit, the resorption of the sponge. Among those are collagenase, its enhancers or inhibitors. Also, a suitable preservative may be used together with the sponge or may be contained in the sponge.

Although a preferred embodiment relates to the use of the hemostatic sponge which contains the activator or proactivator of blood coagulation as the only active component, further substances that influence the velocity of blood coagulation, hemostasis and quality of the sealing, such as tensile strength, strength of the product to tissue, and durability might be comprised.

Procoagulants that enhance or improve the intrinsic or extrinsic coagulation, such as factors or cofactors of blood coagulation, factor XIII, tissue factor, prothrombin complex, activated prothrombin complex, or parts of the complexes, a prothrombinase complex, phospholipids and calcium ions, might be used. In case of a surgical procedure where a precise sealing is needed, it might be preferable to prolong the working period after the hemostatic sponge is applied to the patient and before clotting is effected. The prolongation of the clotting reaction will be ensured, if the sponge according to the invention further comprises inhibitors of blood coagulation in appropriate amounts. Inhibitors, such as antithrombin III optionally together with heparin, or any other serine protease inhibitor, are preferred.

It is also preferred to have such additives, in particular the thrombin or a precursor of thrombin evenly distributed in the material in order to prevent local instability or hyperco-agulability of the material. Even with a certain water content the thrombin activity is surprisingly stable, probably because of the intimate contact of thrombin and collagen in the homogeneous mixture. Nevertheless, thrombin stabilizers preferably selected from the group consisting of a polyol, a polysaccharide, a polyalkylene glycol, amino acids or mixtures thereof might be used according to the invention. The exemplary use of sorbitol, glycerol, polyethylene glycol, polypropylene glycol, mono- or disaccharides such as glucose or saccharose or any sugar or sulfonated amino acid capable of stabilizing thrombin activity is preferred.

According to a further embodiment of the present invention an adhesive layer is attached to the inventive sponge in order to improve adherence of the sponge to a tissue or wound. Such adhesive materials suitable for a sponge for use as a hemostat are e.g. disclosed in the WO2008/016983 (incorporated herein by reference in its entirety). Preferred adhesives mediate adjunctive hemostasis by themselves, and can be suitable to mechanically seal areas of leakage. Such adhesives are for example bioresorbable polymers, in particular polymers that cross-link and solidify upon exposure to body fluids. In further embodiments the adhesive is resorbable and/or biocompatible and can be degraded by a subject, in particular a human subject, in less than 6 months, less than 3 Months, less than 1 month or less than 2 weeks.

"Adhesive" should be understood in the sense that it adheres or binds to a biological tissue and may or may not bind to other materials. A special adhesive layer may comprise a first cross-linkable component, a second cross-linkable component that cross-links with the first cross-linkable component under reaction enabling conditions, wherein the first and second cross-linkable component cross-link to form a porous matrix having interstices. The adhesive layer may further comprise a hydrogel-forming component, which is capable of being hydrated to form a hydrogel to fill at least some of the interstices. Such an adhesive material is disclosed in the WO 2008/016983 (incorporated herein by reference). The first cross-linkable component can include multiple nucleophilic groups and the second cross-linkable component can include multiple electrophilic groups. Upon contact with a biological fluid, or in other reaction enabling conditions, the cross-linkable first and second components cross-link to form a porous matrix having interstices. The hydrogel-forming component can be e.g. a polymer, in particular a biopolymer including polysaccharides or proteins. The hydrogel-forming component is preferably selected from material as being capable of being hydrated to form a biocompatible hydrogel that comprises gelatine and will absorb water when delivered to a moist tissue target side. Such a hydrogel forming component is e.g. the particulate material of the sponge. In some aspects, the first cross-linkable component of the adhesive includes a multi-nucleophilic polyalkylene oxide having m nucleophilic groups, and the second cross-linkable component includes a multi-electrophilic polyalkylene oxide. The multi-nucleophilic polyalkylene oxide can include two or more nucleophilic groups, for example $NH_2$, —SH, —H, —$PH_2$, and/or —CO—NH—$NH_2$. In some cases, the multi-nucleophilic polyalkylene oxide includes two or more primary amino groups. In some cases, the multi-nucleophilic polyalkylene oxide includes two or more thiol groups. The multi-nucleophilic polyalkylene oxide can be polyethylene glycol or a derivative thereof. In some cases, the polyethylene glycol includes two or more nucleophilic groups, which may include a primary amino group and/or a thiol group. The multi-electrophilic polyalkylene oxide can include two or more electrophilic groups such as $CO_2N(COCH_2)_2$, —$CO_2H$, —CHO, —$CHOCH_2$, —N=C=O, —$SO_2CH=CH_2$, $N(COCH)_2$, and/or —S—S—($C_5H_4N$). The multi-electrophilic polyalkylene oxide may include two or more succinimidyl groups. The multi-electrophilic polyalkylene oxide may include two or more maleimidyl groups. In some cases, the multi-electrophilic polyalkylene oxide can be a polyethylene glycol or a derivative thereof.

In special embodiments the first and/or second cross-linkable component is/are synthetic polymers, preferably comprising polyethyleneglycols (PEG) or derivatives thereof. The polymer can be a derivative of PEG comprising active side groups suitable for cross-linking and adherence to a tissue. Preferably, the adhesive comprises succinimidyl, maleimidyl and/or thiol groups. In a two polymer set-up, one polymer may have succinyl or maleimidyl groups and a second polymer may have thiol groups which can attach to the groups of the first polymer. These or additional groups of the adhesive may facilitate the adherence to a tissue.

The adhesive layer can be continuously or discontinuously coated on at least one side of the sponge. However, to allow contact of any body fluids at an injury with the main sponge material, i.e. the fibrous biomaterial and the particulate material it is preferred to place the adhesive layer onto the sponge in a discontinuous manner, e.g. it is possible to place a grid or any other mask onto the sponge and only fill the interstices with the adhesive material and subsequently remove the grid, leaving accessible areas to the collagen sponge matrix. Continuous coatings can be preferable for administration in low bleeding conditions.

In a further aspect of the invention it is also possible to provide a supporting layer with greater tensile strength than the matrix material on at least one side of the sponge. Preferably, the supporting layer is on the opposite side from the adhesive layer. When used, the supporting layer does not face the injury and may or may not be an active hemostatic layer. In principle, it can be of any material providing physical resistance to the sponge. It can be selected from similar materials as the matrix material or the particulate Material. Nevertheless, it may be beneficial if the supporting layer comprises a bioresorbable polymer, as with any other layer, in particular if the complete sponge should be bioresorbable.

The supporting layer may comprise collagen or gelatin, in particular cross-linked gelatin or collagen. In order to improve tensile strength and mechanical support of the sponge matrix it is preferred that the supporting layer is of greater density than the matrix material.

The present invention also provides a wound coverage comprising a sponge according to the invention. The sponge and all additional layers can be provided in a ready to use wound coverage in suitable dimensions. The sponge and/or the coverage preferably has a thickness of at least 1 mm or at least 3 mm or at least 5 mm and/or up to 20 mm, depending on the indication. When the relatively thick flexible sponge is applied to a wound it is important that blood and fibrinogen can be absorbed throughout the sponge before fibrin is formed that might act as a barrier for the absorption of further wound secret.

Another aspect of the invention relates to a method of manufacturing a hemostatic porous sponge comprising providing a fluid of a fibrous biomaterial and suspended particles of a fluid absorbing, particulate material, and drying said fluid with the suspended particles, thereby obtaining a hemostatic porous sponge comprising a matrix fibrous biomaterial and particles of a fluid absorbing, particulate material adhered to said matrix material. Drying may include freeze drying or air drying and comprises removing volatile components of the fluid.

The pH of the fluid, in particular in the case of aqueous solutions may be at least 6, up to 9. Preferred pH ranges are neutral, preferably between 6 and 9 or between 7 and 8. Likewise, it is preferred if the particulate material reacts pH neutral in contact with an aqueous solvent:

One advantage of the inventive particles is that, after being formed from pH neutral solutions, a sponge material will also react in a pH neutral manner in contact with an aqueous solvent. "pH neutral" is considered to increase, or alternatively also decrease, the pH by not more than 1, preferably not more than 0.5 For such a test e.g. equal amounts (mass) of particles and water, preferably without buffer substances, can be used.

In preferred embodiments the solvent is aqueous, i.e. containing water, or pure water, i.e. no other liquid solvent is present. Solvents may comprise water, alcohol, including methanol, ethanol, propanol, butanol, isopropanol, ketones, such as acetone, DMSO, etc. The solvent may or may not further comprise further compounds such as additives, emulsifiers, detergents and wetting agents. If such compounds are used, it is preferred that they are water removable and do not form stable and remaining complexes with the fibrous sponge matrix or the particulate material. The additional compounds may be acidic, preferably neutral or basic.

The preparation of the suspension and/or the fibrous biomaterial (e.g. a collagen gel) can be carried out at room temperature but also at lower (close to 0° C.) or higher temperatures (close to 40° C.) and any temperature range in between as well as even lower or higher temperatures. Thus, in preferred embodiments any one of the method steps is performed between 0° C. and 40° C. or between 15° C. and 30° C.

Any additional layer, e.g. the adhesive layer or the supportive layer can be attached to the dried matrix. However it is also possible to co-dry the additional layer and thus obtain a composite sponge, e.g. if the supportive layer can be constituted from a fluid or gel of a polymer, e.g. a fibrous biomaterial like collagen similar to the matrix material. The matrix of the sponge with the suspended particles can be placed onto said supportive material fluid (or vice versa) and both fluids can be dried in one step. If the concentration of the polymer in the fluid for the supportive material is greater than for the fibrous matrix, usually a layer with greater density may be obtained. Preferably, the collagen fluid for the sponge matrix has a concentration of from 0.1% to 5% (w/w-%), preferably between 0.1% to 1%, most preferably about 0.2%. The concentration of the polymer, in particular collagen, for the supportive layer may be e.g. of from 0.5% to 5% (w/w-%), preferably 0.5% to 2%, most preferred between 15 to 2%. In order to keep these layers separate it is possible to first apply a first fluid into a suitable container, freeze said fluid and apply a second fluid, etc. Such a container can then be freeze-dried to obtain the solid sponge.

In a further aspect the present invention provides a hemostatic porous sponge obtainable by the method according to the invention described above. All preferred embodiments mentioned above for a hemostatic sponge can also be read to this obtainable sponge.

The present invention also provides a method of treating an injury comprising administering a hemostatic porous sponge comprising a matrix of fibrous biomaterial and a fluid absorbing, particulate material adhered to said matrix material to the site of injury. This treatment is in particular suitable for fluid containment. The treatment may comprise sealing the injury in order to prevent further fluid leakage. The injury may comprise a wound, a hemorrhage, damaged tissue, bleeding tissue and/or a leakage of body fluids.

Also provided is a kit for preparing a wound coverage, comprising a sponge as herein disclosed and pharmaceutically active substances. This kit and its components are in particular for the manufacture of a medical sponge for the treatment of an injury as mentioned above.

The present invention is further exemplified by the following examples without being limited thereto.

EXAMPLES

Example 1

Collagen Sponge Containing Cross-Linked Gelatin Particles

A homogeneous suspension containing 80 mg/ml of cross-linked gelatin particles and 2.1 mg/ml of collagen is prepared by stirring. This suspension is filled into a tray (layer thickness 3.5 mm) and freeze-dried. A collagen sponge containing entrapped cross-linked gelatin particles is obtained.

Example 2

Collagen Sponge Containing Cross-Linked Gelatin Particles Discontinuously Coated with an Adhesive Layer A collagen sponge containing cross-linked gelatin particles is prepared according to example 1. After freeze-drying a grid is laid onto the obtained product. 14 mg/cm$^2$ of a 1:1 (w/w) powder mixture of two cross-linkable polyethyleneglycol polymers (PEG-A and PEG-B) are applied over the grid onto the pad. Only the holes of the grid are covered by the powder mixture. The powder is fixed on the pad by short (2-5 min) heating at a temperature higher than the melting point of the PEG components. The grid is removed and a pad with a discontinuous reactive PEG-coating is obtained. PEG-A is a PEG-succinimidyl powder, PEG-B is a PEG-thiol powder.

Example 3

Hemostatic Pad Composed of the Composition Described in example 2 enforced by an additional supporting collagen layer. A 3.5 mm thickness layer of a 10 mg/ml of collagen suspension is filled into a tray and frozen at −20° C. for 1 h. The frozen collagen layer is coated by a 3.5 mm layer of the mixture described in example 3. The two layers are subsequently freeze-dried and the upper layer coated discontinuously with cross-linkable PEG components as described in example 2. The obtained layered pad has more mechanical robustness than the pads described in examples 1 and 2.

Example 4

Hemostasis with the Product Produced According to Example 1

A liver surface abrasion model for hemostasis on heparinized (2×ACT) pigs is used in order to test the hemostatic properties of the pads produced in example 1. With a flat, round, rotating abrasion tool a circular bleeding wound is created on the surface of heparinized pigs. A pad (3×3 cm) is applied dry onto the bleeding wound and hold in place by slightly pressing with saline wetted gauze for 2 min. After 2 min the bleeding is stopped. Within the next 1 min no rebleeding is observed. Blood coagulation within the pad is observed. After 3 min the pad is removed from the site of application with the aid of a forceps. Only a slight adherence to the site of application is observed.

Example 5

Hemostasis with the Product Produced According to Example 2

The pad described in example 2 is applied in the same animal hemostasis model and in the same way as described in example 4, with the discontinuous reactive PEG-coating facing the wound. 2 and 3 min after application no bleeding is observed. Blood enters the pad by the non-coated areas and coagulates within the pad. It is not possible to easily remove the pad 3 min after application from the site of application without disrupting the hemostatic seal. The adherence caused by the reactive PEG-coating is stronger than the internal tensile strength of the pad.

Example 6

Hemostasis with the Product Produced According to Example 3

The pad described in example 3 is applied in the same animal hemostasis model and in the same way as described in example 4, with the discontinuous reactive PEG-coating facing the wound. Hemostasis is obtained in the same way as described in example 5. The additional collagen layer covers as a smooth sheet the hemostatic collagen/cross-linked gelatin layer. Adherence to the wound surface is similar as in example 5.

The invention claimed is:

1. A hemostatic porous sponge comprising a matrix of a fibrous biomaterial comprising collagen and particles of a fluid absorbing particulate material comprising a cross-linked polymer adhered to said matrix material, wherein the sponge further comprises an adhesive layer consisting of a first cross-linkable component and a second cross-linkable component configured to cross-link with the first cross-linkable component under reaction enabling conditions, and wherein the sponge is configured to absorb a fluid into the fluid absorbing particulate material while the fibrous biomaterial matrix remains intact.

2. The sponge according to claim 1, wherein said particulate material is a hemostatic material.

3. The sponge according to claim 2, wherein said particulate material comprises gelatin, fibrin, collagen or any mixture thereof.

4. The sponge according to claim 1 further comprising thrombin or a precursor of thrombin.

5. The sponge according to claim 1, wherein said first and/or second cross-linkable component is PEG or a derivative thereof.

6. The sponge according to claim 1, wherein said adhesive comprises succinimidyl or maleimidyl and thiol or amino groups.

7. The sponge according to claim 1, wherein said adhesive layer is discontinuously coated on at least one side of the sponge.

8. The sponge according to claim 1 being freeze-dried or airdried.

9. The sponge according to claim 1 comprising a supporting layer with greater tensile strength than the matrix material.

10. The sponge according to claim 9, wherein said supporting layer comprises a bioresorbable polymer.

11. The sponge according to claim 9, wherein said supporting layer comprises a greater density than the matrix material.

12. The sponge according to claim 1, wherein the particles of fluid absorbing particulate material are entrapped within the matrix.

13. The sponge according to claim 1, wherein a ratio of particles of fluid absorbing particulate material to matrix material is about 40:1.

14. The sponge according to claim 1, wherein the particles of fluid absorbing particulate material comprise cross-linked gelatin particles.

15. The sponge according to claim 1, wherein the matrix material and particles of fluid absorbing particulate material are present together as a pad, and the adhesive layer is fixed on the pad.

16. The sponge according to claim 15, wherein the adhesive layer is present as a dry layer that has been previously melted as a coating on the pad.

17. The sponge according to claim 15, wherein the adhesive layer is present as a discontinuous coating on the pad.

18. The sponge according to claim 15, wherein the adhesive layer is present as a discontinuous reactive coating on the pad.

19. The sponge according to claim 1, wherein the adhesive layer is in a 1:1 ratio of the first cross-linkable component to the second cross-linkable component.

20. The sponge according to claim 1, wherein the adhesive layer is a mixture of the first cross-linkable component and the second cross-linkable component.

21. The sponge according to claim 1, wherein the adhesive layer is present as a reactive coating.

22. The sponge according to claim 1, wherein the first cross-linkable component is a powder of PEG having reactive succinimidyl functional groups.

23. The sponge according to claim 1, wherein the second cross-linkable component is a powder of PEG having reactive thiol functional groups.

24. The sponge according to claim 1, wherein the sponge is configured to effect hemostasis within 3 minutes after application to a bleeding site.

25. A method of manufacturing a hemostatic porous sponge comprising:
   providing a fluid of a fibrous biomaterial comprising collagen and suspended particles of a fluid absorbing, particulate material comprising a cross-linked polymer,
   drying said fluid with the suspended particles, thereby obtaining a hemostatic porous sponge comprising a matrix of a fibrous biomaterial and particles of a fluid absorbing, particulate material adhered to said matrix material, wherein the sponge is configured to allow the absorbance of fluid into the fluid absorbing particulate material while the fibrous biomaterial matrix remains intact, and
   affixing an adhesive layer to the dried sponge, the adhesive layer consisting of a first cross-linkable component and a second cross-linkable component configured to cross-link with the first cross-linkable component under reaction enabling conditions.

26. A hemostatic porous sponge obtainable by a method according to claim 25.

27. Method of treating an injury comprising administering a hemostatic porous sponge comprising a matrix of a fibrous biomaterial comprising collagen, a fluid absorbing, particulate material comprising a cross-linked polymer adhered to said matrix material, and an adhesive layer consisting of a first cross-linkable component and a second cross-linkable component configured to cross-link with the first cross-linkable component under reaction enabling conditions to the site of injury, wherein fluid from the injury is absorbed into the fluid absorbing particulate material while the fibrous biomaterial matrix remains intact.

28. The method according to claim 27, wherein said injury comprises a wound, a hemorrhage, damaged tissue and/or bleeding tissue.

29. The sponge according to claim 27, wherein the sponge is configured to effect hemostasis within 3 minutes after application to a bleeding site.

* * * * *